US007854957B2

(12) United States Patent  
Diaz et al.

(10) Patent No.: US 7,854,957 B2
(45) Date of Patent: Dec. 21, 2010

(54) SYSTEMS AND METHODS FOR PRODUCING A MEDICAL DEVICE

(75) Inventors: Stephen Hunter Diaz, Palo Alto, CA (US); Kenneth Joel den Dulk, Mountain View, CA (US)

(73) Assignee: Innovational Holdings, LLC, New Brunswick, NJ (US)

( * ) Notice: Subject to any disclaimer, the term of this patent is extended or adjusted under 35 U.S.C. 154(b) by 331 days.

(21) Appl. No.: 11/669,035

(22) Filed: Jan. 30, 2007

(65) Prior Publication Data

US 2008/0095917 A1 Apr. 24, 2008

Related U.S. Application Data

(60) Provisional application No. 60/829,902, filed on Oct. 18, 2006.

(51) Int. Cl.
*A61L 33/00* (2006.01)
(52) U.S. Cl. .............. 427/2.1; 623/1.42; 623/1.11; 623/1.39; 427/2.24; 427/2.25; 427/421.1; 427/424; 427/425; 427/427.4; 427/427.5
(58) Field of Classification Search ............... 623/1.42, 623/1.11; 427/2.24
See application file for complete search history.

(56) References Cited

U.S. PATENT DOCUMENTS

| 2,695,595 | A | 11/1954 | Hagerman |
|---|---|---|---|
| 3,031,059 | A | 4/1962 | Ingham, Jr. |
| 3,876,465 | A | 4/1975 | Prazak, III |
| 3,920,131 | A | 11/1975 | Gebel |
| 4,733,665 | A | 3/1988 | Palmaz |
| 4,739,762 | A | 4/1988 | Palmaz |
| 4,776,337 | A | 10/1988 | Palmaz |
| 4,969,458 | A | 11/1990 | Wiktor |
| 5,464,650 | A | 11/1995 | Berg et al. |
| 5,538,126 | A | 7/1996 | Rhodes |
| 5,759,192 | A | 6/1998 | Saunders |

(Continued)

FOREIGN PATENT DOCUMENTS

EP 0540290 B1 5/1993

(Continued)

OTHER PUBLICATIONS

Office Action in U.S. Appl. No. 11/669,045, mailed Sep. 17, 2009.

(Continued)

*Primary Examiner*—Michael Barr
*Assistant Examiner*—Andrew Bowman

(57) ABSTRACT

A machine and process useful for processing a delicate workpiece, e.g., an implantable medical device, includes a carrier having a mandrel and wheels. The work piece is positioned on the mandrel, which is free to roll by gravity on rails which cooperate with the wheels to self-align the travel of the carrier. The carrier can move the workpieces through a series of processing steps by gravity feed and without human intervention. A laterally movable carriage receives the rolling carriers and moves the carrier for processing, and returns the carrier to the rails to again roll by gravity to another processing substation for additional processing. An elevator, which can including processing units itself, is positioned along the rails to receive carriers and raise them so they can continue to roll for further processing.

22 Claims, 10 Drawing Sheets

U.S. PATENT DOCUMENTS

| | | |
|---|---|---|
| 5,780,807 A | 7/1998 | Saunders |
| 5,836,964 A | 11/1998 | Richter et al. |
| 5,906,759 A | 5/1999 | Richter |
| 5,972,180 A | 10/1999 | Chujo |
| 5,992,000 A | 11/1999 | Humphrey et al. |
| 5,997,703 A | 12/1999 | Richter |
| 6,066,168 A | 5/2000 | Lau et al. |
| 6,114,049 A | 9/2000 | Richter |
| 6,126,376 A | 10/2000 | Peterson |
| 6,131,266 A | 10/2000 | Saunders |
| 6,153,252 A | 11/2000 | Hossainy et al. |
| 6,197,048 B1 | 3/2001 | Richter |
| 6,240,616 B1 | 6/2001 | Yan |
| 6,241,762 B1 | 6/2001 | Shanley |
| 6,249,952 B1 | 6/2001 | Ding |
| 6,257,706 B1 | 7/2001 | Ahn |
| 6,273,913 B1 * | 8/2001 | Wright et al. .............. 623/1.42 |
| 6,299,755 B1 | 10/2001 | Richter |
| 6,334,807 B1 | 1/2002 | Lebel et al. |
| 6,369,355 B1 | 4/2002 | Saunders |
| 6,375,826 B1 | 4/2002 | Wang et al. |
| 6,378,988 B1 | 4/2002 | Taylor et al. |
| 6,395,326 B1 | 5/2002 | Castro et al. |
| 6,482,166 B1 | 11/2002 | Fariabi |
| 6,497,916 B1 | 12/2002 | Taylor et al. |
| 6,548,308 B2 | 4/2003 | Ellson et al. |
| 6,599,415 B1 | 7/2003 | Ku et al. |
| 6,616,765 B1 | 9/2003 | Castro et al. |
| 6,645,547 B1 | 11/2003 | Shekalim et al. |
| 6,676,987 B2 | 1/2004 | Zhong et al. |
| 6,679,980 B1 | 1/2004 | Andreacchi |
| 6,682,771 B2 | 1/2004 | Zhong et al. |
| 6,689,159 B2 | 2/2004 | Lau et al. |
| 6,695,920 B1 | 2/2004 | Pacetti et al. |
| 6,713,132 B2 | 3/2004 | Sashihara |
| 6,723,373 B1 | 4/2004 | Narayanan et al. |
| 6,746,686 B2 | 6/2004 | Hughes et al. |
| 6,783,793 B1 | 8/2004 | Hossainy et al. |
| 6,790,228 B2 | 9/2004 | Hossainy et al. |
| 6,818,063 B1 | 11/2004 | Kerrigan |
| 6,860,946 B2 | 3/2005 | Hossainy et al. |
| 6,861,088 B2 | 3/2005 | Weber et al. |
| 6,865,810 B2 | 3/2005 | Stinson |
| 6,866,810 B2 | 3/2005 | Ahmed et al. |
| 6,867,389 B2 | 3/2005 | Shapovalov et al. |
| 6,887,510 B2 | 5/2005 | Villareal |
| 6,927,359 B2 | 8/2005 | Kleine et al. |
| 6,948,223 B2 | 9/2005 | Shortt |
| 6,952,086 B1 | 10/2005 | Krefta et al. |
| 6,955,723 B2 | 10/2005 | Pacetti et al. |
| 6,957,152 B1 | 10/2005 | Esbeck |
| 6,981,985 B2 | 1/2006 | Brown et al. |
| 7,037,552 B2 | 5/2006 | Zhong et al. |
| 2002/0082680 A1 | 6/2002 | Shanley et al. |
| 2003/0088307 A1 | 5/2003 | Shulze et al. |
| 2003/0157241 A1 | 8/2003 | Hossainy et al. |
| 2003/0175410 A1 | 9/2003 | Campbell et al. |
| 2004/0073294 A1 * | 4/2004 | Diaz et al. .................. 623/1.42 |
| 2004/0127976 A1 | 7/2004 | Diaz |
| 2004/0127977 A1 | 7/2004 | Shanley |
| 2004/0220660 A1 | 11/2004 | Shanley et al. |
| 2004/0220665 A1 | 11/2004 | Hossainy et al. |
| 2005/0010282 A1 * | 1/2005 | Thornton et al. ........... 623/1.42 |
| 2005/0061771 A1 | 3/2005 | Murphy |
| 2005/0064088 A1 | 3/2005 | Fredrickson |
| 2005/0069630 A1 | 3/2005 | Fox et al. |
| 2005/0079274 A1 | 4/2005 | Palasis et al. |
| 2005/0106210 A1 | 5/2005 | Ding et al. |
| 2005/0160891 A1 | 7/2005 | Koch |
| 2005/0166389 A1 | 8/2005 | Perreault et al. |
| 2005/0222676 A1 | 10/2005 | Shanley et al. |
| 2005/0229670 A1 | 10/2005 | Perreault |
| 2005/0233062 A1 | 10/2005 | Hossainy et al. |
| 2005/0240256 A1 | 10/2005 | Austin |
| 2005/0261757 A1 | 11/2005 | Shanley |
| 2005/0273161 A1 | 12/2005 | Malik et al. |
| 2006/0096660 A1 | 5/2006 | Diaz et al. |
| 2006/0177564 A1 | 8/2006 | Diaz et al. |
| 2007/0259099 A1 * | 11/2007 | Van Sciver ................. 427/2.24 |

FOREIGN PATENT DOCUMENTS

| | | |
|---|---|---|
| EP | 0734699 B1 | 10/1996 |
| EP | 0853927 B1 | 7/1998 |
| EP | 0956832 B1 | 11/1999 |
| EP | 0770401 B1 | 11/2002 |
| EP | 1493456 A2 | 1/2005 |
| EP | 1518570 B1 | 3/2005 |
| EP | 0846447 B1 | 6/2005 |
| EP | 1559439 B1 | 8/2005 |
| EP | 1341479 B1 | 10/2005 |
| EP | 0973462 B1 | 6/2006 |
| WO | WO9833546 A1 | 8/1998 |
| WO | WO9937245 A1 | 7/1999 |
| WO | WO0226162 A2 | 4/2002 |
| WO | WO0243788 A2 | 6/2002 |
| WO | WO03048665 A1 | 6/2003 |
| WO | 2004/037126 A2 | 5/2004 |
| WO | WO2004094096 A1 | 11/2004 |
| WO | WO2004096093 A1 | 11/2004 |
| WO | WO2004096311 A1 | 11/2004 |
| WO | WO2005016187 A1 | 2/2005 |
| WO | WO2005016396 A1 | 2/2005 |
| WO | WO2005018606 A1 | 3/2005 |
| WO | WO2005034805 A1 | 4/2005 |
| WO | WO2005034806 A1 | 4/2005 |
| WO | WO2005037444 A1 | 4/2005 |
| WO | WO2005037447 A1 | 4/2005 |
| WO | WO2005047572 A1 | 5/2005 |
| WO | WO2005089951 A1 | 9/2005 |
| WO | WO2005092420 A1 | 10/2005 |
| WO | WO2005102590 A1 | 11/2005 |
| WO | WO2005112570 A2 | 12/2005 |
| WO | WO2006012034 A2 | 2/2006 |

OTHER PUBLICATIONS

Office Action mailed Nov. 23, 2009 in U.S. Appl. No. 11/669,018.
U.S. Appl. No. 11/668,988, Stephen Hunter Diaz, filed Jan. 30, 2007.
U.S. Appl. No. 11/669,018, Stephen Hunter Diaz, filed Jan. 30, 2007.
U.S. Appl. No. 11/669,045, Stephen Hunter Diaz, filed Jan. 30, 2007.

* cited by examiner

_US 7,854,957 B2_

SYSTEMS AND METHODS FOR PRODUCING A MEDICAL DEVICE

This application claims priority under 35 U.S.C. §119 to U.S. Provisional Application No. 60/829,902, filed 18 Oct. 2006, by the inventors hereof, the entirety of which incorporated by reference herein. This application is related, but does not claim priority, to U.S. Ser. No. 11/668,988, filed Jan. 30, 2007; U.S. Ser. No. 11/669,018, filed Jan. 30, 2007; and U.S. Ser. No. 11/669,045, filed Jan. 30, 2007; all three of which also claim priority under 35 U.S.C. §119 to U.S. Provisional Application No. 60/829,902, filed 18 Oct. 2006.

FIELD OF THE INVENTION

The invention relates to a method and apparatus for loading a beneficial agent, such as a drug into or onto an expandable medical device, and more particularly, the invention relates to a method and apparatus for dispensing a beneficial agent into an expandable medical device such as a stent.

DESCRIPTION OF THE RELATED ART

Implantable medical devices are often used for delivery of a beneficial agent such as a drug, to an organ or tissue in the body at a controlled delivery rate over an extended period of time. These devices may deliver agents to a wide variety of bodily systems to provide a wide variety of treatments.

One of the many implantable medical devices which have been used for local delivery of beneficial agents is the coronary stent. Coronary stents are typically introduced percutaneously, and transported transluminally until positioned at a desired location. These devices are then expanded either mechanically, such as by the expansion of a mandrel or balloon positioned inside the device, or expand themselves by releasing stored energy upon actuation within the body. Once expanded within the lumen, these devices, called stents, become encapsulated within the body tissue and remain a permanent implant.

Known stent designs include monofilament wire coil stents (U.S. Pat. No. 4,969,458); welded metal cages (U.S. Pat. Nos. 4,733,665 and 4,776,337); and, most prominently, thin-walled metal cylinders with axial slots formed around the circumference (U.S. Pat. Nos. 4,733,665; 4,739,762; and 4,776,337). Known construction materials for use in stents include polymers, organic fabrics and biocompatible metals, such as stainless steel, cobalt chromium alloys, gold, silver, tantalum, titanium, and shape memory alloys, such as Nitinol.

Of the many problems that may be addressed through stent-based local delivery of beneficial agents, one of the most important is restenosis. Restenosis is a major complication that can arise following vascular interventions such as angioplasty and the implantation of stents. Simply defined, restenosis is a wound healing process that reduces the vessel lumen diameter by extracellular matrix deposition, neointimal hyperplasia, and vascular smooth muscle cell proliferation, and which may ultimately result in renarrowing or even reocclusion of the lumen. To treat this condition, additional revascularization procedures are frequently required, thereby increasing trauma and risk to the patient.

One of the techniques under development to address the problem of restenosis is the use of surface coatings of various beneficial agents on stents. Surface coatings, however, can provide little actual control over the release kinetics of beneficial agents. These coatings are necessarily very thin, typically 5 to 8 microns deep. The surface area of the stent, by comparison is very large, so that the entire volume of the beneficial agent has a very short diffusion path to discharge into the surrounding tissue.

Increasing the thickness of the surface coating has the beneficial effects of improving drug release kinetics including the ability to control drug release and to allow increased drug loading. However, the increased coating thickness results in increased overall thickness of the stent wall. This is undesirable for a number of reasons, including increased trauma to the vessel wall during implantation, reduced flow cross-section of the lumen after implantation, and increased vulnerability of the coating to mechanical failure or damage during expansion and implantation. Coating thickness is one of several factors that affect the release kinetics of the beneficial agent, and limitations on thickness thereby limit the range of release rates, duration of drug delivery, and the like that can be achieved.

In addition to sub-optimal release profiles, there are further problems with surface coated stents. The fixed matrix polymer carriers frequently used in the device coatings typically retain approximately 30% of the beneficial agent in the coating indefinitely. Since these beneficial agents are frequently highly cytotoxic, sub-acute and chronic problems such as chronic inflammation, late thrombosis, and late or incomplete healing of the vessel wall may occur. Additionally, the carrier polymers themselves are often highly inflammatory to the tissue of the vessel wall. On the other hand, use of biodegradable polymer carriers on stent surfaces can result in the creation of "virtual spaces" or voids between the stent and tissue of the vessel wall after the polymer carrier has degraded, which permits differential motion between the stent and adjacent tissue. Resulting problems include micro-abrasion and inflammation, stent drift, and failure to re-endothelialize the vessel wall.

Another significant-problem is that expansion of the stent may stress the overlying polymeric coating causing the coating to plastically deform or even to rupture, which may therefore effect drug release kinetics or have other untoward effects. Further, expansion of such a coated stent in an atherosclerotic blood vessel will place circumferential shear forces on the polymeric coating, which may cause the coating to separate from the underlying stent surface. Such separation may again have untoward effects including immobilization of coating fragments causing vascular obstruction.

In addition, it is not currently possible to deliver some drugs with a surface coating due to sensitivity of the drugs to water, other compounds, or conditions in the body which degrade the drugs. For example, some drugs lose substantially all their activity when exposed to water for a period of time. When the desired treatment time is substantially longer than the half life of the drug in water, the drug cannot be delivered by known coatings. Other drugs, such as protein or peptide based therapeutic agents, lose activity when exposed to enzymes, pH changes, or other environmental conditions. These drugs which are sensitive to compounds or conditions in the body often cannot be delivered using surface coatings.

Accordingly, it would be desirable to provide an apparatus and method for loading a beneficial agent into an expandable medical device, such as a stent, for delivery of agents, such as drugs, to a patient.

U.S. Patent Application Publication No. 2004/0073294, published Apr. 15, 2004, ("the '294 application"), which is incorporated by reference herein in its entirety, describes a process of filling reservoirs (e.g., holes) in stents with beneficial agents. While the systems and processes described in the '294 publication have proven very useful and expedient, some aspects thereof can be improved upon. The stent filling process described in the '294 publication requires the use of a mandrel to support the stents during the filling process. The mandrel is made of very straight wire, covered with soft rubber. The stents are slipped onto the mandrel and then slightly crimped to seal off their interior surface. When filling solution is injected into the stent hole, it is contained in the reservoir formed by the stent hole and the mandrel surface.

The mandrels are mounted on metal carriers that contain simple "V" bearings with spring levers to hold the mandrel against the bearing surfaces. The carrier is manually mounted into a filing station of the machine during the filling process. After filling, the carrier is manually removed from the machine and placed in an oven for drying. Consequently, hundreds of these carriers are used and reused.

While this system has worked well, there are several limitations:

1. Insertion and removal from the machine and oven must be done by hand and is therefore slow and expensive.

2. Placement of the carriers with their mandrels into the machine relies on the operator skill, and so is not always perfect. This causes error in shooting material into or onto the stents carried on the mandrel.

3. Since many carriers are needed, their total cost is relatively high. To keep the cost down, fabrication tolerances must be fairly loose and the materials must be inexpensive. Thus, each of the carriers is slightly different due to fabrication tolerances. This can contribute to errors in shooting.

4. As the carriers move about the manufacturing facility, they are invariably damaged, despite efforts to avoid mishandling, which compromises their accuracy.

What is therefore also needed is a mandrel "carrier" that allows automatic loading and unloading, with precision bearings which are aligned with great accuracy in the machine, without any intervention from the operator.

SUMMARY OF THE INVENTION

According to a first aspect of the invention, a method of processing a medical device, the method comprises performing a first operation (A) or (B) on said medical device at a first elevation, wherein operation (A) comprises depositing a material onto or into the medical device, and operation (B) comprises a process selected from the group consisting of drying, irradiating, heating, and combinations thereof, gravity feeding said medical device to a second elevation lower than said first elevation; and performing a second operation (A) or (B) on said medical device at said second elevation.

According to another aspect of the present invention, a processing system useful for processing at least one medical device mounted on at least one mandrel comprises a first substation (A) configured and arranged to deposit a material onto or into the at least one medical device, a second substation (B) configured and arranged to perform a process on said at least one medical device, selected from the group consisting of drying, irradiating, heating, and combinations thereof, and an automatic transport system configured and arranged to transport said at least one mandrel between said first substation and said second substation.

Still other aspects, features, and attendant advantages of the present invention will become apparent to those skilled in the art from a reading of the following detailed description of embodiments constructed in accordance therewith, taken in conjunction with the accompanying drawings.

BRIEF DESCRIPTION OF THE DRAWINGS

The invention of the present application will now be described in more detail with reference to exemplary embodiments of the apparatus and method, given only by way of example, and with reference to the accompanying drawings, in which:

FIG. 2 illustrates an enlarged cross-sectional view of a portion of the stent of FIG. 1a;

FIG. 8d illustrates an enlarged, outside side view of a portion of the station illustrated in FIGS. 5 and 8a;

DETAILED DESCRIPTION OF EXEMPLARY EMBODIMENTS

Figure 1A:
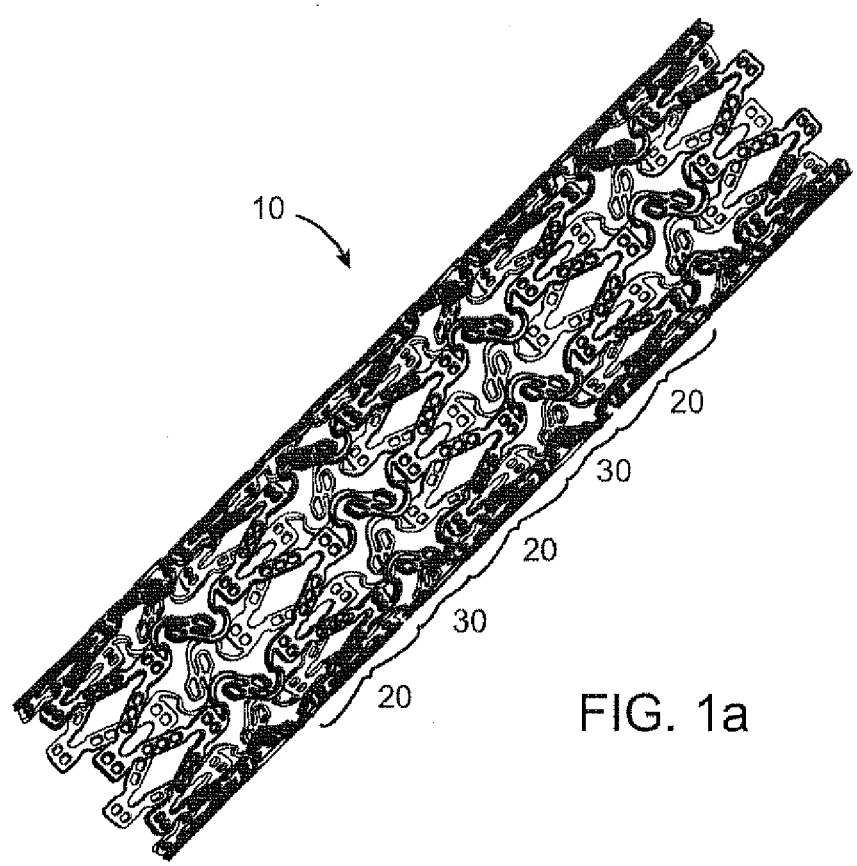
FIG. 1a illustrates an enlarged perspective view of one example of a stent according to the present invention in a semi expanded configuration.

A machine and process useful for processing a delicate workpiece, e.g., an implantable medical device, includes a carrier having a mandrel and wheels. The workpiece is positioned on the mandrel, which is free to roll by gravity on rails which cooperate with the wheels to self-align the travel of the carrier. The carrier can move the workpieces through a series of processing steps by gravity feed and without human intervention. A laterally movable carriage receives the rolling carriers and moves the carrier for processing, and returns the carrier to the rails to again roll by gravity to another processing substation for additional processing. An elevator, which can including processing units itself, is positioned along the rails to receive carriers and raise them so they can continue to roll for further processing.

Referring to the drawing figures, like reference numerals designate identical or corresponding elements throughout the several figures.

First, the following terms, as used herein, shall have the following meanings:

The term "beneficial agent" as used herein is intended to have its broadest possible interpretation and is used to include any therapeutic agent or drug, as well as inactive agents such as barrier layers, carrier layers, therapeutic layers or protective layers.

The terms "drug" and "therapeutic agent" are used interchangeably to refer to any therapeutically active substance that is delivered to a body of a living being to produce a desired, usually beneficial, effect. The present invention is particularly well suited for the delivery of antineoplastic, angiogenic factors, immuno-suppressants, anti-inflammatories and antiproliferatives (anti-restenosis agents) such as paclitaxel and Rapamycin for example, and antithrombins such as heparin, for example.

The term "matrix" or "biocompatible matrix" are used interchangeably to refer to a medium or material that, upon implantation in a subject, does not elicit a detrimental response sufficient to result in the rejection of the matrix. The matrix typically does not provide any therapeutic responses itself, though the matrix may contain or surround a therapeutic agent. A matrix is also a medium that may simply provide support, structural integrity or structural barriers. The matrix may be polymeric, non-polymeric, hydrophobic, hydrophilic, lipophilic, amphiphilic, and the like.

The term "bioresorbable" refers to a matrix, as defined herein, that can be broken down by either chemical or physical process, upon interaction with a physiological environment. The bioresorbable matrix is broken into components that are metabolizable or excretable, over a period of time from minutes to years, preferably less than one year, while maintaining any requisite structural integrity in that same time period.

The term "polymer" refers to molecules formed from the chemical union of two or more repeating units, called monomers. Accordingly, included within the term "polymer" may be, for example, dimers, trimers and oligomers. The polymer may be synthetic, naturally-occurring or semisynthetic. In preferred form, the term "polymer" refers to molecules which typically have a $M_w$ greater than about 3000 and preferably greater than about 10,000 and a $M_w$ that is less than about 10 million, preferably less than about a million and more preferably less than about 200,000.

The term "openings" refers to holes of any shape and includes both through-openings and recesses.

Implantable Medical Devices with Holes

Figure 1B:
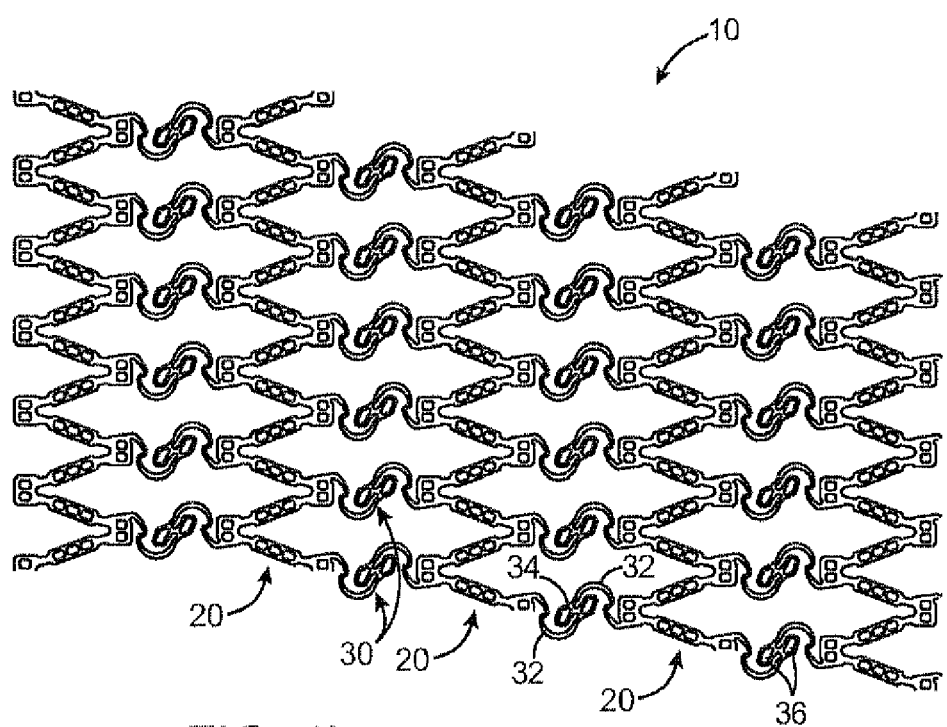
FIG. 1b illustrates a portion of the stent of FIG. 1a, unrolled and laid flat.

FIGS. 1a and 1b illustrate a stent 10 formed from a plurality of expandable rings 20 and a plurality of flexible bridging elements 30 connecting the rings. The stent 10 is expandable from an insertion configuration to an expanded implanted configuration by deployment of an expanding device, such as a balloon catheter. The expandable rings 20 provide radial hoop strength to the stent while the flexible bridging elements 30 allow the stent to flex axially during delivery and upon implantation. The flexible bridging elements 30 are designed with elements having varying widths contoured to distribute strain substantially uniformly along the bridging elements. The contoured shapes of the bridging elements 30 maximize fatigue strength and flexibility of the bridging elements.

The term "width" as used herein means a dimension of an element in a plane of the cylindrical surface of the stent. The width is generally measured along a line substantially perpendicular to the edges of the element.

In the embodiment illustrated in FIGS. 1a and 1b, the expandable rings are formed by a plurality of struts 22 and a plurality of ductile hinges 24 arranged such that upon expansion, the ductile hinges are deformed while the struts are not substantially deformed. Openings 60 formed in the struts receive a beneficial agent which may include a therapeutic agent and a bioresorbable polymer. The ductile hinge 24 and strut 22 structures are described in further detail in U.S. Pat. No. 6,241,762 which is incorporated herein by reference in its entirety. As shown in FIGS. 1a and 1b, the rings 20 have alternating open and closed ends. In the arrangement of FIGS. 1a and 1b, the closed ends of the rings 20 are aligned with closed ends of adjacent rings and the closed ends are interconnected by the flexible bridging elements 30. The adjacent closed ends can be referred to as structures which are substantially 180 degrees out of phase. The expandable rings may alternatively be formed in any of the other known ring structures including serpentine rings, diamond structures, chevron shapes, or the like which are in phase or out of phase.

The flexible bridging elements 30 of the stent 10 of FIGS. 1a and 1b have been designed to maximize fatigue strength and flexibility. The bridging element 30 includes two curved flex members 32 each connecting an adjacent expandable ring 20 to a central reservoir containing structure 34. The central reservoir containing structure 34 and the openings therein may take on many different shapes depending on the space available and the amount of drug to be delivered from the reservoirs. In the example of FIGS. 1a and 1b, the reservoir containing structure 34 includes two irregular polygonal openings 36 arranged partially within the arch shapes formed by the curved flex members 32. Further details of stent 10 are provided in U.S. Published Application No. 2005/0261757, the entirety of which is incorporated by reference herein.

The volume of beneficial agent that can be delivered using reservoirs as described herein is about 3 to 10 times greater than the volume of a 5 micron coating covering a stent with the same stent/vessel wall coverage ratio. This much larger beneficial agent capacity provides several advantages. The larger capacity can be used to deliver multi-drug combinations, each with independent release profiles, for improved efficacy. Also, larger capacity can be used to provide larger quantities of less aggressive drugs and to achieve clinical efficacy without the undesirable side-effects of more potent drugs, such as retarded healing of the endothelial layer.

Figure 2:
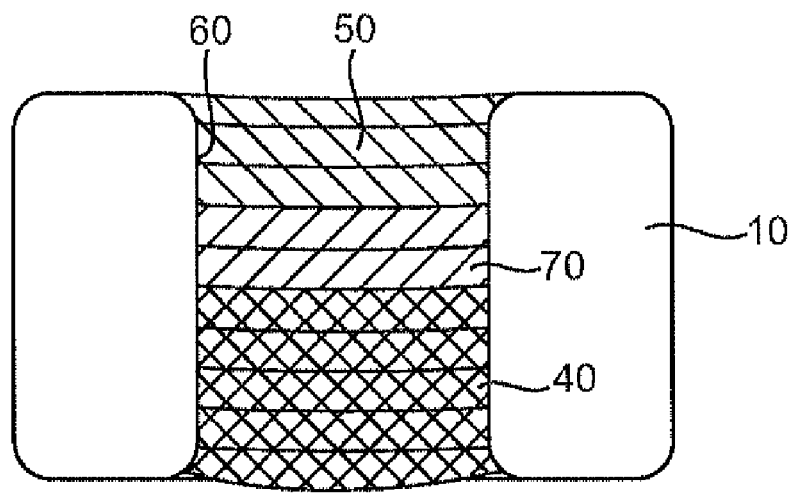

FIG. 2 shows a cross-section of a medical device 10 in which one or more beneficial agents have been loaded into the opening 60 in multiple deposits. Examples of some methods of creating such deposits and arrangements of deposits are described in U.S. patent application Ser. No. 09/948,989, filed on Sep. 7, 2001, which is incorporated herein by reference in its entirety. Although the deposits are illustrated as discrete layers, the deposits can also mix together upon delivery to result in an inlay of beneficial agent with concentration gradients of therapeutic agents but without distinct boundaries between deposits.

According to one example, the total depth of the opening 60 is about 100 to about 140 microns, typically 125 microns (0.0032 inches) and the typical deposit thickness would be about 2 to about 50 microns, preferably about 12 microns. Each typical deposit is thus individually about twice as thick as the typical coating applied to surface-coated stents. There would be at least two and preferably about ten to twelve such deposits in a typical opening, with a total beneficial agent thickness about 25 to 28 times greater than a typical surface coating. According to one preferred embodiment of the present invention, each of the openings have an area of at least $5 \times 10^{-6}$ inch$^2$, and preferably at least $8 \times 10^{-6}$ inch$^2$, and more preferably about $12\text{-}15 \times 10^{-6}$ inch$^2$. Typically, the openings are filled about 50% to about 75% full of beneficial agent.

Since each deposit is created independently, individual chemical compositions and pharmacokinetic properties can be imparted to each deposit. Numerous useful arrangements of such deposits can be formed, some of which will be described below. Each of the deposits may include one or more agents in the same or different proportions from one deposit to the next. The deposits may be solid, porous, or filled with other drugs or excipients. As mentioned above, although the deposits are deposited separately, they may mix forming an inlay without boundaries between deposits.

As shown in FIG. 2, the opening 60 is filled with a beneficial agent. The beneficial agent includes a base 40, a therapeutic agent 70, and a cap 50.

Alternatively, different deposits could be comprised of different therapeutic agents altogether, creating the ability to release different therapeutic agents at different points in time. The sequential deposits of beneficial agent provide the ability to tailor a delivery profile to different applications. This allows the medical device according to the present invention to be used for delivery of different beneficial agents to a wide variety of locations in the body.

A protective layer in the form of a cap 50 is provided at a tissue contacting surface of a medical device. The cap 50 can block or retard biodegradation of subsequent deposits and/or blocks or retards diffusion of the beneficial agent in that direction for a period of time which allows the delivery of the medical device to a desired location in the body. When the medical device 10 is a stent which is implanted in a lumen, the base 40 is positioned on a side of the opening 20 facing the inside of the lumen. The base 40 prevents the therapeutic agent 30 from passing into the lumen and being carried away without being delivered to the lumen tissue.

Typical formulations for therapeutic agents incorporated in these medical devices are well known to those skilled in the art.

Medical devices and stents, as described herein, are useful for the prevention of amelioration of restenosis, particularly after percutaneous transluminal coronary angioplasty and intraluminal stent placement. In addition to the timed or sustained release of anti-restenosis agents, other agents such as anti-inflammatory agents may be incorporated into the multi-layers incorporated in the plurality of holes within the device. This allows for site-specific treatment or prevention any complications routinely associated with stent placements that are known to occur at very specific times after the placement occurs.

Uses for Implantable Medical Devices

Although the present invention has been described with reference to a medical device in the form of a stent, the medical devices of the present invention can also be medical devices of other shapes useful for site-specific and time-release delivery of drugs to the body and other organs and tissues. The drugs may be delivered to the vasculature including the coronary and peripheral vessels for a variety of therapies, and to other lumens in the body. The drugs may increase lumen diameter, create occlusions, or deliver the drug for other reasons.

Methods and Systems for Loading a Beneficial Agent in a Medical Device

Figure 3:
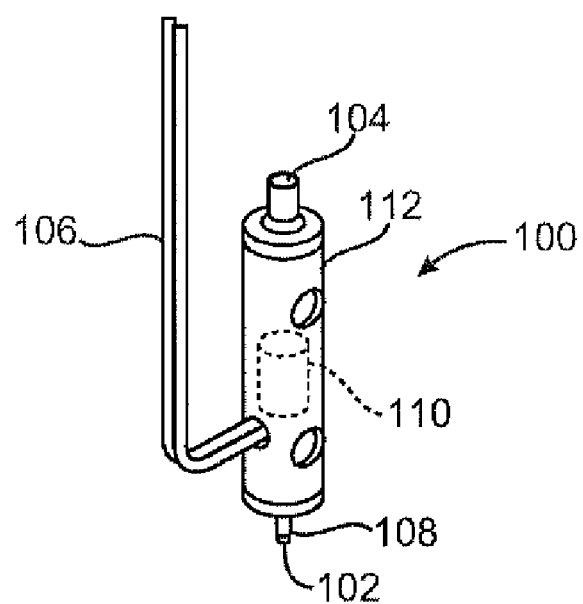
FIG. 3 illustrates a perspective illustration of an exemplary microjet device which forms a part of the present invention.

FIG. 3 shows a piezoelectric micro-jetting dispenser 100 used to dispense a beneficial agent into the opening of a medical device. The dispenser 100 has a capillary tube 108 having a fluid outlet or orifice 102, a fluid inlet 104, and an electrical cable 106. The piezoelectric dispenser 100 preferably includes a piezo crystal 110 within a housing 112 for dispensing a fluid droplet through the orifice 102. The crystal 110 surrounds a portion of the capillary tube 108 and receives an electric charge that causes the crystal to vibrate. When the crystal vibrates inward, it forces a tiny amount of fluid out of the fluid outlet 102 of the tube 108 to fill an opening 20 in a medical device. In addition, when the crystal vibrates outward, the crystal pulls additional fluid into the tube 108 from a fluid reservoir connected to the inlet 104 to replace the fluid that has been dispensed into the opening of the medical device.

In one embodiment as shown in FIG. 3, the micro-jetting dispenser 100 includes an annular piezoelectric (PZT) actuator 110 bonded to a glass capillary 108. The glass capillary 108 is connected at one end to a fluid supply (not shown) and at the other end has an orifice 102 generally in the range of about 0.5 to about 150 microns, and more preferably about 30 to about 60 microns. When a voltage is applied to the PZT actuator, the cross-section of the capillary glass 108 is reduced/increased producing pressure variations of the fluid enclosed in the glass capillary 108. These pressure variations propagate in the glass capillary 108 toward the orifice 102. The sudden change in cross-section (acoustic impedance) at the orifice 102, causes a droplet to be formed. This mode of producing droplets is generally called drop on demand (DOD).

In operation, the micro-jetting dispenser 100, depending on the viscosity and contact angle of the fluid, can require either positive or negative pressure at the fluid inlet 104. Typically, there are two ways to provide pressure at the fluid inlet 104. First, the pressure at the fluid inlet 104 can be provided by either a positive or a negative head by positioning of the fluid supply reservoir. For example, if the fluid reservoir is mounted only a few millimeters above the dispenser 100, a constant positive pressure will be provided. However, if the fluid reservoir is mounted a few millimeters below the dispenser 100, the orifice 102 will realize a negative pressure.

Alternatively, the pressure of the fluid at the inlet 104 can be regulated using existing compressed air or vacuum sources. For example, by inserting a pressure vacuum regulator between the fluid source and the dispenser 100, the pressure can be adjusted to provide a constant pressure flow to the dispenser 100.

In addition, a wide range of fluids including beneficial agents can be dispensed through the dispenser 100. The fluids preferably have a viscosity of no greater than about 40 centipoise. The droplet volume of the dispenser 100 is a function of the fluid, orifice 102 diameter, and actuator driving parameter (voltage and timing) and usually ranges from about 50 picoliters to about 200 picoliters per droplet. If a continuous droplet generation is desired, the fluid can be pressurized and a sinusoidal signal applied to the actuator to provide a continuous jetting of fluids. Depending on the beneficial agent dispensed, each droplet may appear more like a filament.

It can be appreciated that other fluid dispensing devices can be used without departing from the present invention. In one embodiment, the dispenser is a piezoelectric microjetting device manufactured by MicroFab Technologies, Inc., of Plano, Tx.

Figure 4:
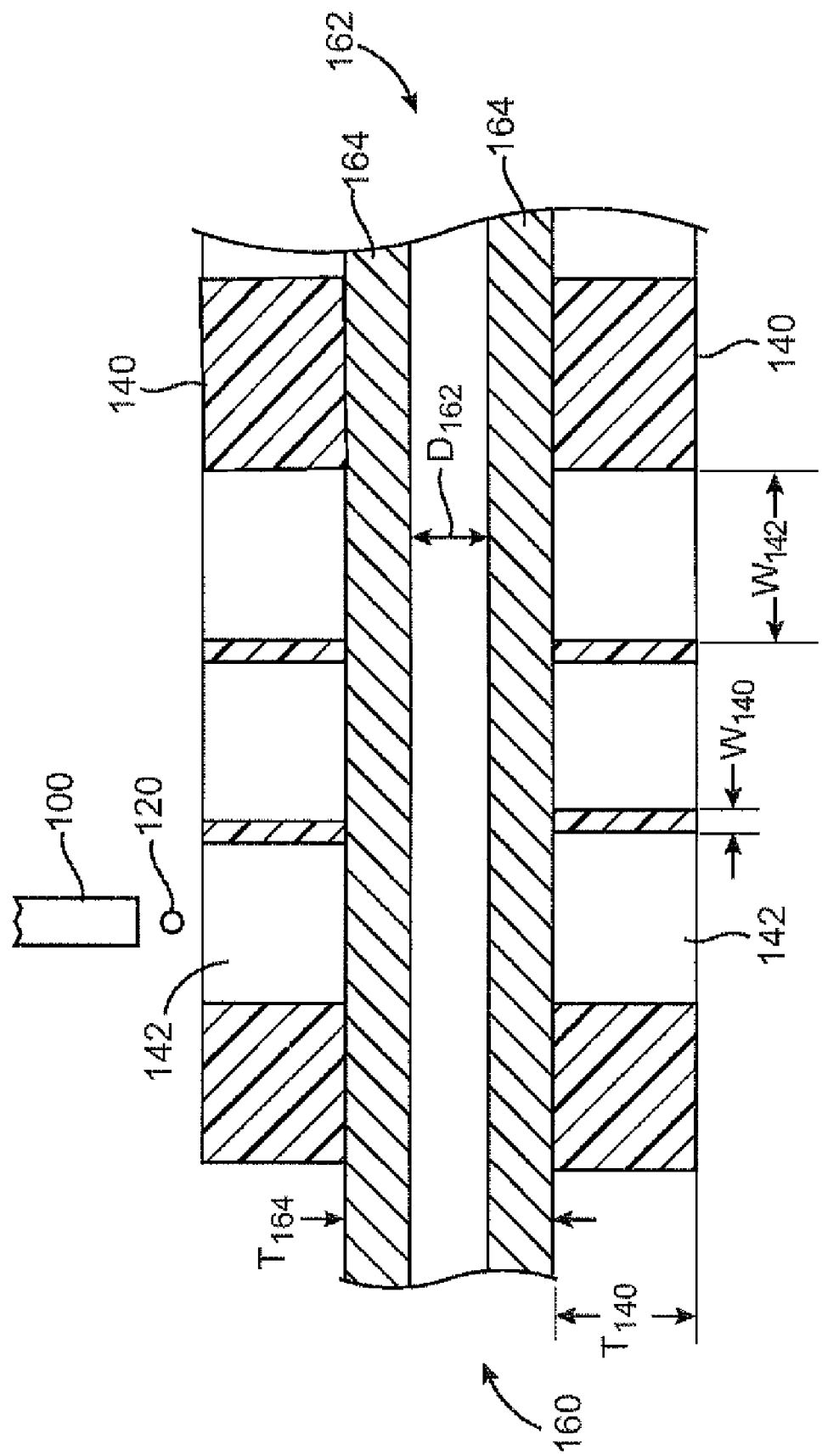
FIG. 4 illustrates an enlarged longitudinal cross-sectional view of an implantable medical device mounted on a mandrel in accordance with the present invention.

The electric cable 106 is preferably connected to associated drive electronics (not shown) for providing a pulsed electric signal. The electric cable 106 provides the electric signal to control the dispensing of the fluid trough the dispenser 100 by causing the crystal to vibrate. FIG. 4 shows an expandable medical device in the form of a stent 140 receiving a droplet 120 of a beneficial agent from a piezoelectric microjetting dispenser 100. The stent 140 is preferably mounted to a mandrel 160. The stent 140 can be designed with large, non-deforming struts and links (as shown in FIG. 1), which contain a plurality of openings 142 without compromising the mechanical properties of the struts or links, or the device as a whole. The openings 142 serve as large, protected reservoirs for delivering various beneficial agents to the device implantation site. The openings 142 can be circular, rectangular, D-shaped, polygonal, or other shaped and form cylindrical, rectangular or other shaped holes extending through the thickness of the stent 140. In addition, openings 142 having a depth less than the thickness of the stent 140 may also be used. It can be appreciated that other shaped holes 142 can be used without departing from the present invention.

The volume of the hole 142 will vary depending on the shape and size of the hole 142. For example, a rectangular shaped opening 142 having a width $W_{142}$ of 0.1520 mm (0.006 inches) and a height/depth $T_{140}$ of 0.1270 mm (0.005 inches) will have a volume of about 2.22 nanoliters. Meanwhile, a round opening having a radius of 0.0699 mm (0.00275 inches) will have a volume of about 1.87 nanoliters. A D-shaped opening having a width of 0.1520 mm (0.006 inches) along the straight portion of the D, has a volume of about 2.68 nanoliters. The openings according to one example are about 0.0813 mm (0.0032 inches) in depth having a slight conical shape due to laser cutting.

Although a tissue supporting device configuration has been illustrated in FIG. 1, which includes ductile hinges, it should be understood that the beneficial agent may be contained in openings in stents having a variety of designs including many of the known stents.

The mandrel 160 can include a wire member 162 encapsulated by an outer jacket 164 of a resilient or a rubber-like material. The wire member 162 may be formed from a metallic thread or wire having a circular cross-section. The metallic thread or wire is preferably selected from a group of metallic threads or wire, including Nitinol, stainless steel, tungsten, nickel, or other metals having similar characteristics and properties. Alternatively, the mandrel 160 can be formed of a pull-truded carbon file rod which is advantageously very stiff; the mandrel optionally can be formed of other materials.

In one example, the wire member 162 has an outer diameter $D_{162}$ of between about 0.889 mm (0.03 inches) and about 0.991 mm (0.04 inches) for use with a cylindrical or implantable tubular device having an outer diameter of about 3 mm (0.118 inches) and an overall length of about 17 mm (0.669 inches). It can be appreciated that the outer diameter of the wire member 162 can vary depending on the size and shape of the expandable medical device 140.

Examples of rubber-like materials for the outer jacket 164 include silicone, polymeric materials, such as polyethylene, polypropylene, polyvinyl chloride (PVC), ethyl vinyl acetate (EVA), polyurethane, polyamides, polyethylene terephthalate (PET), and their mixtures and copolymers. However, it can be appreciated that other materials for the outer jacket 164 can be implemented, including those rubber-like materials known to those skilled in the art.

In one embodiment, the wire member 162 is encapsulated in a tubular outer jacket 164 having an inner diameter of about 0.635 mm (0.25 inches) and a thickness $T_{164}$ of about 0.5 mm. The outer jacket 164 can be mounted over the wire member 162 by inflating the tubular member to increase to a size greater than the outer diameter of the wire member 162. The tubular member can be inflated using an air pressure device known to those skilled in the art. The wire member 162 is placed inside of the outer jacket 164 by floating the outer jacket 164 of silicon over the wire member 162 over a cushion of pressurized air. However, it can be appreciated that the wire member 162 can be encapsulated in an outer jacket of silicon or other rubber-like material by any method known to one skilled in the art.

In one embodiment for loading stents having a diameter of about 3 mm (0.118 inches), a wire member 162 having an outer diameter $D_{162}$ of 0.939 mm (0.037 inches) is selected. In one example, the wire member 162 is about 6-24 inches, preferably about 8-16 inches, in length, and about 3-12 stents are placed on the mandrel. The outer jacket 164 has an inner diameter of about 0.635 mm (0.025 inches).

The expandable medical device or stent 140 is then loaded onto the mandrel 160 in any method known to one skilled in the art. In one embodiment, the stents 140 and the mandrel 160 are dipped into a volume of lubricant to lubricate the stents 140 and the mandrel 160. The stents 140 are then loaded onto the mandrel 160. The drying of the stents 140 and the mandrel 160 create a substantially firm fit of the stents 140 onto the mandrel 160. Alternatively, or in addition to drying, the stents 140 can be crimped onto the mandrel by a method known to one skilled in the art onto the mandrel 160. The crimping ensures that the stents 140 will not move or rotate during mapping or filling of the openings. By way of further non-limiting example, the distance $W_{140}$ between openings 142 in the stent is 0.001-0.01 inches, depending on the location, the width $W_{142}$ of opening 142 is about 0.002-0.009 inches, and the thickness $T_{140}$ of the stent is about 0.003 inches (0.08 mm).

Figure 5:
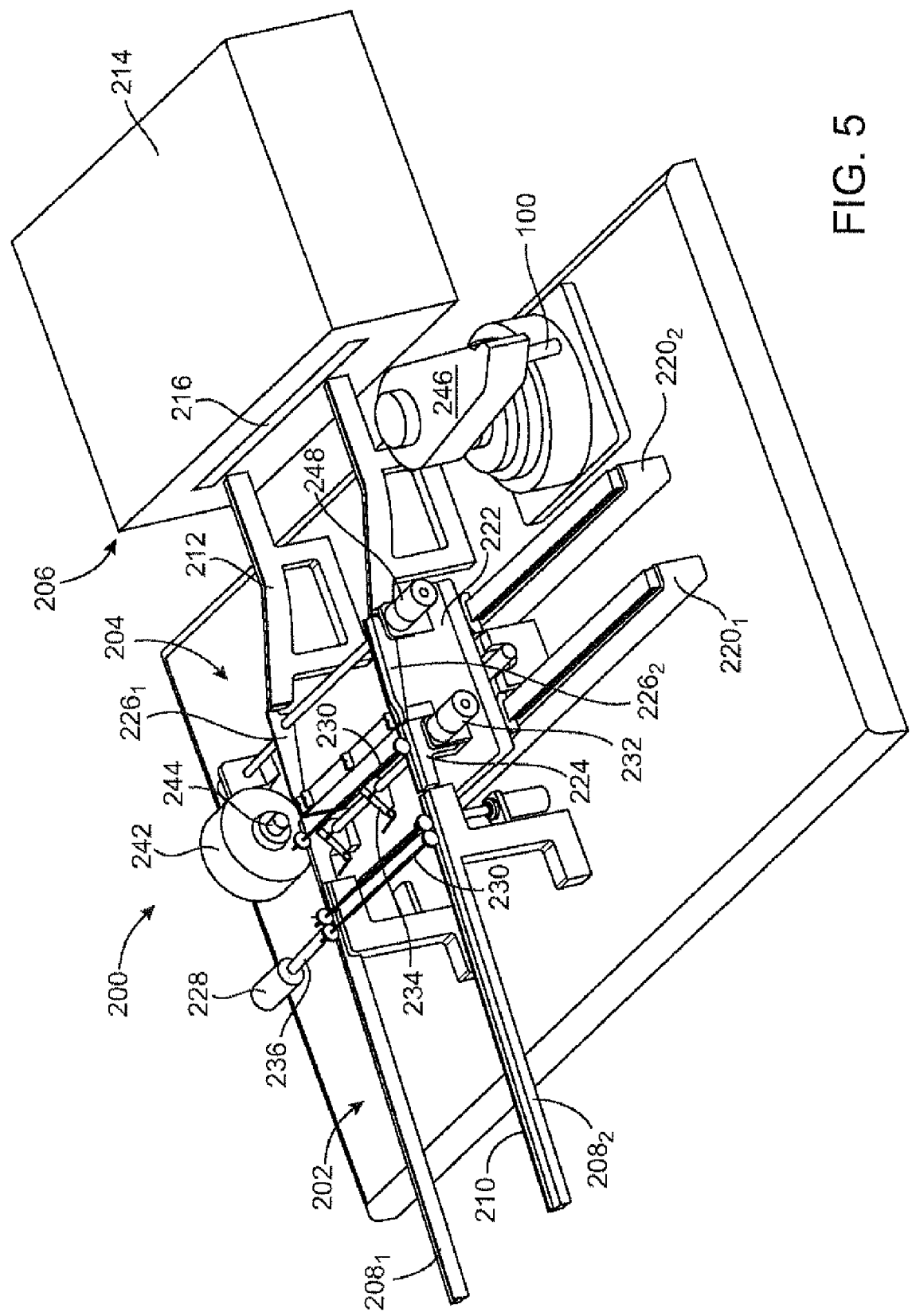
FIG. 5 illustrates a perspective view of an exemplary processing station in accordance with the present invention.

Turning now to FIG. 5, processes and apparatus embodying further principles of the present invention are illustrated. In general terms, FIG. 5 illustrates a processing station 200 useful for processing a workpiece which benefits from the use of a simple, elegant, and invariable phenomenon: gravity. More specifically, the station 200 advances the workpiece, here a delicate medical device, through the station by gravity feed. By incorporation of further optional steps and structures of the present invention, the gravity feed of the workpiece is performed without exposing the exterior surface of the workpiece to contact with the processing apparatus, which can greatly reduce damage to the workpiece during processing.

Before embarking on a detailed explanation of the various components and subcomponents of the apparatus illustrated in FIG. 5, it is to be understood that the following is a description of merely exemplary devices and processes which embody one or more principles of the present invention.

The processing station 200 generally includes several substations, namely, an input substation 202, a processing substation 204, and an output substation 206. While only a single processing substation 204 is illustrated in FIG. 5, the present invention is not so limited, and the processing station 200 can include a plurality of serially arranged processing substations 204 positioned between the input 202 and the output 206.

Figure 6:
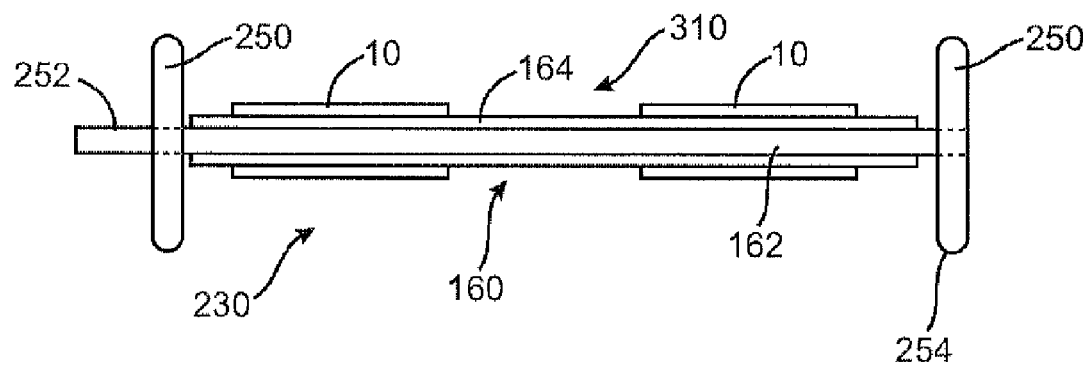
FIG. 6 illustrates an enlarged view of a carrier in accordance with the present invention.
Figure 7:
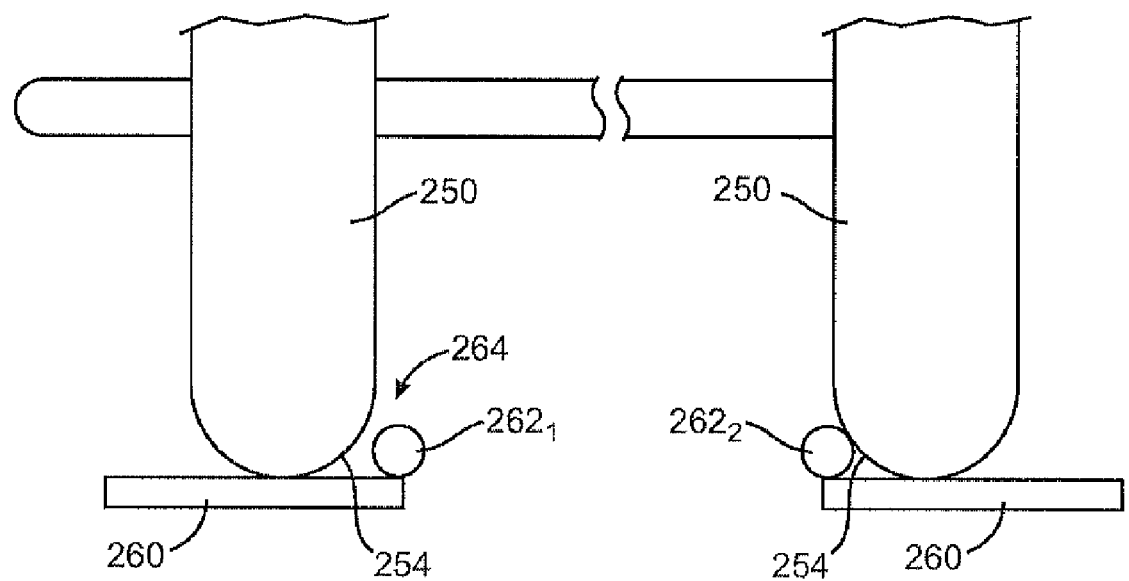
FIG. 7 schematically illustrates an enlarged view of the function of some portions of a device according to the present invention.

Before further exposition on the several exemplary substations, a description of an exemplary workpiece carrier 230, which passes through the several substations, will be useful. Turning briefly to FIGS. 6 and 7, a carrier 230 is illustrated. Because of the similarity between some of the subcomponents of the carrier 230 with subcomponents described above with reference to FIGS. 1-4, the same reference numerals have been used to designate the same or similar structures. The carrier 230 includes a mandrel 160 which includes a wire 162 sheathed in a jacket or covering 164 over a portion of its length. One or more workpieces, in this exemplary embodiment tubular implantable medical devices 10, are positioned on the sheath 164, preferably forming at least one unoccupied space 310 between the workpieces. Also mounted on the mandrel 160 are at least two, and optionally more, wheels 250. It is particularly advantageous when only two wheels are mounted on each mandrel 160, because of the benefits that flow from the explanation below of the function of the wheels 250. Thus, the carrier 230 can take the form of an axle with wheels. Providing wheels 250 on the carriers permits the wheels to maintain spacing between the mandrels 160 on adjacent carriers, because the wheels are larger than the workpiece(s) mounted on the mandrels.

As illustrated in FIG. 6, it is useful when one of the wheels (in this exemplary embodiment, that illustrated on the left in FIG. 6) is mounted at a position spaced from the end of the mandrel 160, such that a free end 252 of the mandrel is left exposed. The free end 252, as will be explained in greater detail below, can be used to manipulate the carrier 230. Another wheel 250 is preferably, although not necessarily, mounted on the opposite end of the mandrel 160 without exposing a free end. The wheels 250 preferably are the same size and configuration.

According to a preferred embodiment, the wheels 250 positioned at or near the ends of the mandrel 160 have a bearing surface 254 which is shaped to assist in realigning the carrier if it becomes misaligned while passing through the various stations of the processing station 200. With reference to FIG. 7, the inventors herein have found that making the bearing surfaces 254 to form a toroidal shape, at least on the inwardly facing portions of the bearing surfaces, permits the wheels to automatically correct a misalignment of the carrier 230. In the highly schematic illustration of FIG. 7, the wheels 250 each rest on a bearing surface 260 of a track or rail, each of which track or rail includes an inner bearing guide $262_1$, $262_2$. The spacing of the wheels 250, that is, the distance between the interior surfaces of the wheels is selected so that it is slightly greater than the distance between the exterior surfaces of the inner bearing guides $262_1$, $262_2$, leaving a small gap 264. That is, the distance between the wheels is greater than the distance between the rails, so that only one wheel touches at one time. Thus, the carrier 230 is free to roll along the surfaces 260 without contacting the inner bearing guides $262_1$, $262_2$. If, however, the carrier 230 rolls such that it becomes misaligned and one of the inner surfaces 254 of one of the wheels 250 contacts the exterior surface of the adjacent inner bearing guide $262_1$, $262_2$, the configuration of the bearing surface 254 and/or that of the exterior surface of the inner bearing guide $262_1$, $262_2$ causes the carrier to roll into a more aligned orientation. More specifically, when a wheel 250 touches the exterior surface of an inner bearing guide $262_1$, $262_2$, that wheel is ahead of the other wheel and rides up on the guide, causing the radius of rotation of that guide-riding wheel to be less than the radius of rotation of the other, non-guide-riding wheel of the carrier 230. The guide-riding wheel thus travels less distance along the surface 260 of the track or rail than the non-guide-riding wheel, for each rotation of the carrier, and therefore the trailing non-guide-riding wheel will catch up with the leading, guide-riding wheel. When the non-guide-riding wheel catches up with the guide-riding wheel, the carrier 230 is re-centered with the track or rail and is again free to roll along the track without bearing against the inner bearing guides $262_1$, $262_2$. In this way, the carrier will continuously self correct for any misalignment and jams are avoided.

Returning to FIG. 5, the input substation 202 includes a rail (or track) 210 for each wheel 250 of the carrier 230; in the exemplary embodiment illustrated in FIG. 5, there are two wheels, and therefore there are two rails $208_1$ and $208_2$. The configuration of the rails 210 will be discussed in greater detail below with reference to FIGS. 8a, 8c, and 8d. The rails 210 are sloped towards the processing substation 204, so that the carriers 230 will freely roll towards the substation 204 without the need for additional devices to propel or otherwise advance the carriers. By way of non-limiting example, the rails 210 are sloped between about 1 and 10 degrees, although larger and smaller slopes are also usable. Each of the rails $208_1$ and $208_2$ is formed with a cross-sectional shape that works with the carriers 230 to self-correct misalignment of the carrier with respect to the rails, as described above, exemplary embodiments of which are discussed with reference to FIG. 8c below.

According to an alternative embodiment exemplifying principles of the present invention, the input substation 202 can be replaced with a cassette (not illustrated) which is removably positioned adjacent to the upstream end of the processing substation 204. Such a cassette is preferably removable and replaceable from the input to the processing substation 204, and is sized to contain one or more carriers 230, and may optionally be environmentally controlled (e.g., heat, atmosphere, light).

The processing substation 204 includes a carriage 222 which slides laterally along one or more rails $220_1$, $220_2$, driven by a servo motor 228 via a shaft 236, e.g., a screw and nut, which is connected to the carriage. The carriage 222 is movable along the rails 220 from the position illustrated in FIG. 5, in which the rails 210 are aligned with the several rails carried by the carriage (see below), to a laterally displaced position at which the carriage is adjacent to a robotic arm 246 which carries (at least) the jet 100 described above. A bridge 224 is mounted to the carriage 222, to which one or more retention spring levers 234 are rotatably mounted, with a motor 232 mounted to rotate the spring lever 234. The bridge 224 spans the gap between the end of the rails 210 and the pick-off rails 226. The bridge 224 can optionally be eliminated and the rails 210, 226 sized to extend across the gap otherwise occupied by the bridge 224, with the motor 232 mounted to the carriage 222 to rotate the spring lever 234. The bridge 224 is described in greater detail below with reference to FIGS. 9 and 10.

At least one, and advantageously several bearings 240 are also mounted to the carriage 222, in lateral alignment with a motorized chuck 242 having an orifice portion 244 that extends towards the bearings and is configured to open and close to grasp the free end 252 of a carrier 230 that rests on the bearings 240. The chuck 242 is also mounted to the carriage 222, so that it moves laterally with the bearings 240. The processing substation 204 also includes a pair of pick-off arms $226_1$, $226_2$, which are pivotally mounted to the carriage 222, the rotation of which is controlled by a motor 248. The pick-off arms 226, described in greater detail with reference to FIGS. 8a, 8d, perform a number of functions: they include an upstream portion that is laterally aligned with the bearings 240, so that a carrier 230 that rolls to the pick-off arms is positioned on the bearings; the motor 248 both lowers the arms out of interference with a carrier when held on the bearings, and raises the arms to pick-up the carrier and cause the carrier to roll towards the output substation 206; the pick-off arm $226_1$ laterally moves the carrier into the chuck 242, while the pick-off arm $226_2$ laterally pulls the carrier out of the chuck; and rails permit a carrier to roll over the pick-off arms towards the output substation in the manner described elsewhere herein.

The output substation 206 is positioned adjacent to the processing substation 204, and includes a set of rails 212 that match, in number and configuration, the rails 210 of the input substation 202, and which are aligned with the corresponding rails of the pick-off arm 226 of the processing substation 204. The rails 210 also downwardly slope toward an elevator 214 having an opening 216 thereto which is aligned with the rails 212. In this manner, once the carriers 230 are released from the processing substation 204, they freely roll down the rails 212 and into the opening 216 of the elevator 214. Having entered the elevator 214, a carrier 230 is moved upwards to increase its potential energy (e.g., its altitude or height) before exiting the elevator for further movement along the processing line by rolling by gravity. In this manner, the carrier 230 can be moved through a series of connected stations 200, with the output (substation) of one leading to the input (substation) of the next, without the need for additional conveying systems. An exemplary embodiment of the elevator 214 is described in greater detail with reference to FIG. 23.

Each of the set of rails described herein (although not necessarily rails 220,) is configured similarly, have the same number of rails, and are aligned so that a carrier 230 can roll from one set of rails to the next by gravity alone.

Figure 8A:
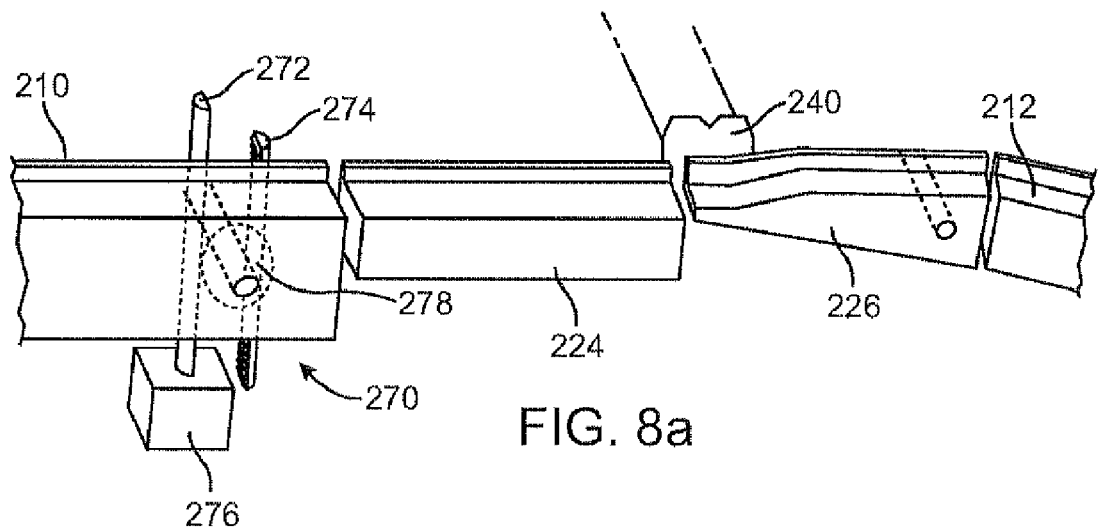
FIG. 8a illustrates an enlarged perspective view of a portion of the station illustrated in FIG. 5.

Turning now to FIG. 8a, the rail 210 of input substation 202, the bridge 224, the pick-off arm 226, one of the bearings 240, and the rail 212 of output substation 206 are illustrated. As discussed above, the respective rails slope downwardly from left to right, permitting a carrier 230 (not illustrated in FIG. 8a) to roll through the several substations. In order to control the number and frequency of carriers 230 through the station 220, that is, the flow of carriers, a singulator 270 is advantageously provided at the downstream end of the input substation 202. Any of numerous forms of singulators can be used for singulator 270, and the present invention is not limited to the particular example described herein. The singulator 270 performs at least two functions: it provides a stop for the carrier(s) 230 rolling down the rails 210 of the input substation 202; and it permits a select number of carriers, preferably one carrier, to roll down to the processing substation 204. By way of non-limiting example, singulator 270 includes a double-rack-and-pinion arrangement, including vertically slidable racks 272, 274, bridged by a rotatable pinion 278. One of the racks 272 is driven vertically by a linear actuator 276. In a well-known manner, vertical movement of the rack 272 by the actuator 276 is translated through the pinion 278 to the rack 274, which moves in the opposite vertical direction in accordance with the pitch of the teeth (not illustrated) on the racks and pinion. According to another exemplary embodiment (not illustrated), the actuator 276 can be a rotational actuator which drives the pinion 278. In use, the rack 272 is normally maintained in an upper position so that the rack 272 interferes with the motion of and stops a carrier 230 rolling along the rail 210. When it is desired to process the workpiece(s) carried on that carrier 230, the actuator 276 is operated to lower the rack 272 and simultaneously raise the rack 274, which permits the lowermost carrier to roll into contact with the rack 274. By spacing the racks 272, 274 an appropriate distance, the presence of a carrier 230 against rack 274 automatically causes the next upstream carrier to be positioned upstream of rack 272, thus ensuring that only one carrier is in position to roll toward the processing substation 204. Then, the actuator 276 is reversed, and the rack 272 moved upward to act as a stop and the rack 274 is lowered to permit the carrier 230 to continue rolling. The lateral (along the length of a carrier) and vertical (whether positioned above or below the plane of motion of the carriers) locations of the singulator 270 can be anywhere, so long as it can control the input of carriers 230 into the processing substation 204.

Figure 8B:
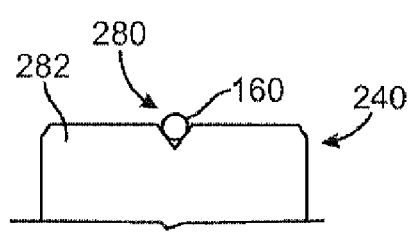
FIG. 8b illustrates an enlarged front view of a bearing in accordance with the present invention.

Also illustrated in FIG. 8a is the general linear alignment of the bearings 240 with the upstream portion of pick-off arm 226. As described in greater detail below, an upstream portion of the pick-off arm 226 is configured to stop a rolling carrier 230 at a location sufficiently close to the bearings 240 that, when the pick-off arm is lowered and no longer supports a carrier, the mandrel 160 of the carrier is lowered into a precision groove of the bearings and is thereby very accurately positioned for further processing. FIG. 8b illustrates an enlarged side elevational view of one of the two or more bearings 240 that are laterally arranged along the carriage 222, and which are aligned with the chuck 242. Each bearing 240 includes a body 282 in the top of which a V-groove is machined, sized to receive the mandrel 160 of a carrier 230 therein. As described above, when a carrier 230 is permitted to roll to the upstream portion of the pick-off arm 226, the mandrel 160 will come to rest in the precision groove of the bearing 240, thus very accurately and reproducibly positioning the workpiece 10 on the carriage 222.

Figure 8C:
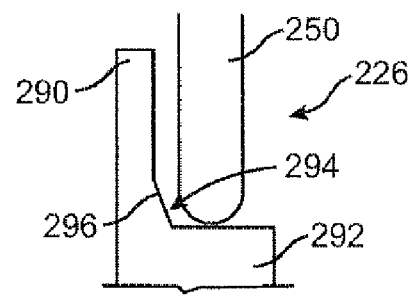
FIG. 8c illustrates an enlarged cross-sectional view, with portions shown in phantom, taken at line VIII-VIII in FIG. 8d, of a rail embodying principles of the present invention.

FIG. 8c illustrates a cross-sectional view of the rails on which the carrier 230 rolls, in this example pick-off arm 226. The rails on which the carrier 230 rolls embody at least principles of the present invention discussed with reference to FIG. 7, above. In the exemplary embodiment of FIG. 8c, a wheel 250 of a carrier 230 is illustrated in phantom to place the carrier in context. The pick-off arm 226 includes an upstanding wall 290 located on the inner portion of a base 292, on the top of which base the wheel can roll. The top surface of the base 292 is advantageously oriented so that in a purely vertical cross section, such as that illustrated in FIG. 8c, the line of the top surface is perpendicular to the local gravity field (i.e., purely horizontal), so that a carrier can roll freely down the rail without drifting to one lateral side or the other. Of course, a longitudinal cross-sectional view (not illustrated) reveals that the rails slope from an upstream portion to a downstream portion (left to right, in these illustrations). The pick-off arm 226 includes a feature 294 which, as discussed above with reference to FIG. 7, assists and/or causes re-alignment of a rolling, misaligned carrier 230. In this non-limiting example, the re-alignment feature includes an angled wall 296 extending at an angle between the upstanding wall 290 and the base 292. Because it is the interaction of the feature 294, in this example wall 296, and the bearing surface 254 of the wheel 250, the exact angle that the wall 296 makes with the upstanding wall 290 (or the top surface of base 292) will differ, depending on the shape of the bearing surface 254. In one example, an angle between the wall 296 and the base 292 between about 60 degrees and about 30 degrees, preferably about 45 degrees, has functioned adequately, although other angles could be used.

Figure 8D:
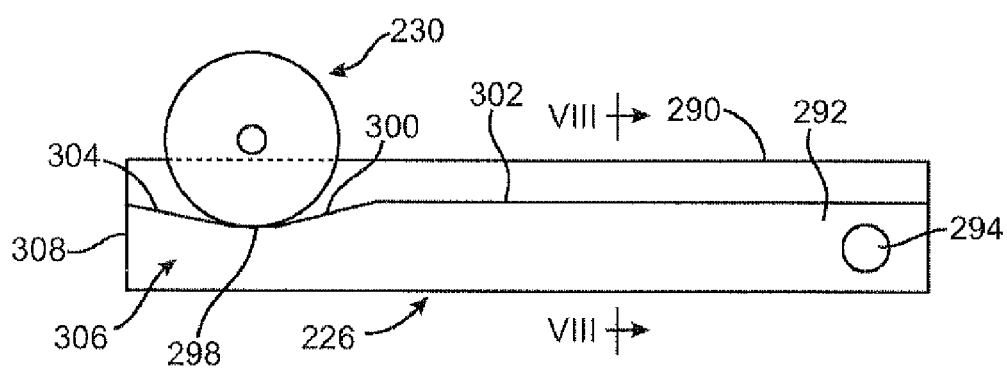

Turning now to FIG. 8d, a right side elevational view of the pick-off arm 226 is illustrated, including a carrier 230 which has been permitted to roll onto the pick-off arm. Wall 290 and base 292 are illustrated, although illustration of the feature 294 has been omitted to simplify the view so as to not obscure aspects of the invention. A shaft 294 extends laterally through and is firmly connected to the pick-off arm near a downstream end of the pick-off arm, to which motor 248 (FIG. 5) is attached and by which the rotation of the motor is translated into rotation of the pick-off arm about the axis of the shaft.

The pick-off arm 226 is provided with a upwardly oriented rolling surface 302, which can be formed on the top of base 292. An upstream portion of the surface 302 includes a well, depression, or the like, 306, which is sized and configured to center a carrier 230 which has rolled onto the pick-off arm 226 and to generally align the mandrel 160 (not illustrated in FIG. 8d) with the precision grooves of the bearings 240. In the exemplary embodiment illustrated in FIG. 8d, the centering feature 306 includes a downward sloping surface 304 and an upward sloping surface 300, which meet at a location 298 which is laterally aligned with the line of the bearings 240. As illustrated in FIG. 8d, the location 298 can itself include a flattened portion or, alternatively, the surfaces 304, 300 can meet at a point and thus form a larger V-groove somewhat like those of the bearings.

Surface 224 (see FIG. 8a) is sloped at an angle sufficient to move the carrier 230 quickly and with enough kinetic energy to overcome small imperfections in the rails and/or wheels. This kinetic energy is thereafter converted to another form of energy, e.g., heat, before the carrier 230 will be at rest. By way of non-limiting example, one way to accomplish this energy conversion is to raise the pick-off arms 226 so that its upstream end surface 308 is presented as a wall to the rolling carrier 230, stopping the carrier completely. Thereafter, the pick-off arms 226 are lowered and the carrier 230 is thus permitted to roll into the valley-like location 298, which quickly centers the carrier in the V-grooves 280.

Figure 9:
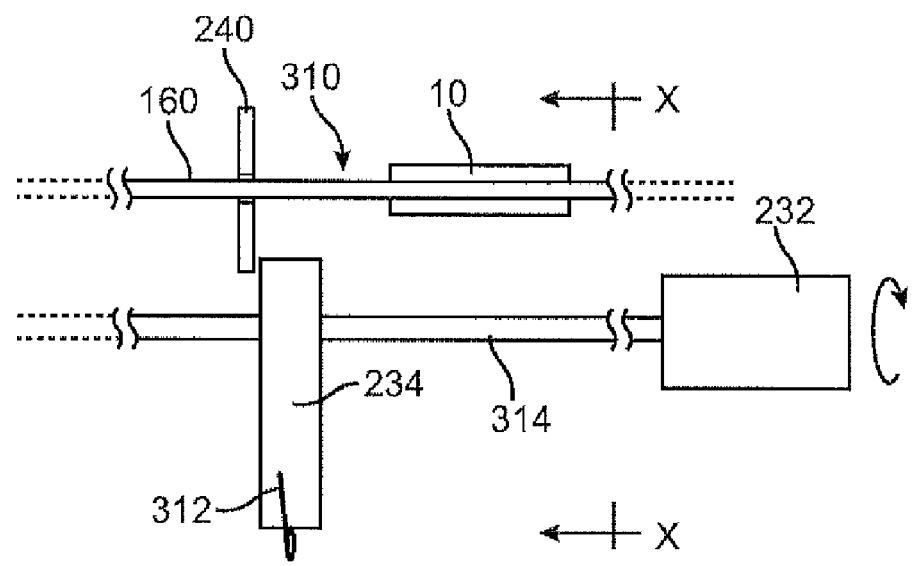
FIG. 9 illustrates a top plan view, with portions broken away, of a carrier and a spring lever in accordance with the present invention.
Figure 10:
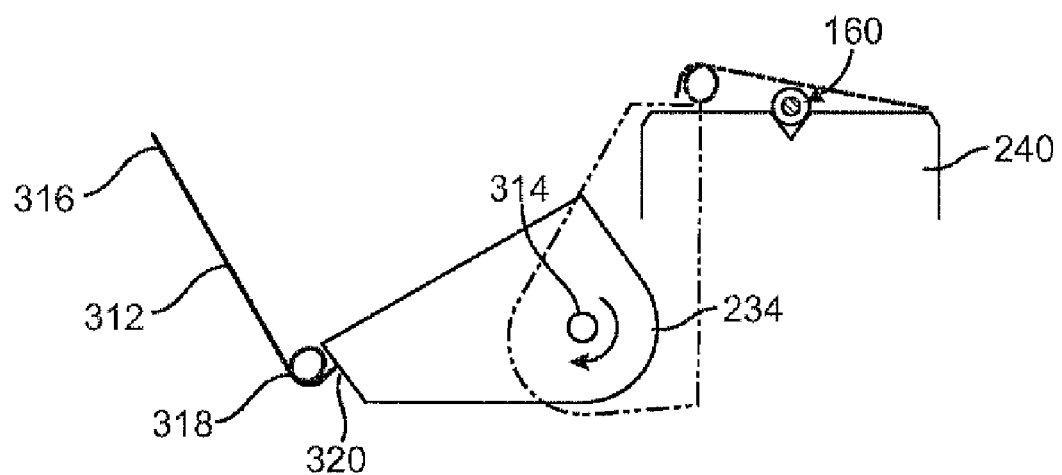
FIG. 10 illustrates a cross-sectional view taken at line X-X in FIG. 9.

FIGS. 9 and 10 illustrate a top plan and a right side elevational view, respectively, of portions of the mandrel 160 and one of one or more laterally spaced spring levers 234. The spring lever or spring levers 234 are mounted on a rotatable shaft 314 which is driven by the motor 232, as described above, and is thus controllable to rotate toward and away from the mandrel 160, as suggested by the arrows in the drawing figures. The spring lever 234 includes an arm 312 attached to the spring lever, as at 320, and extends between a coiled portion 318 and a straight portion 316. The straight portion 316 extends in a direction and a length sufficient so that, when the spring lever 234 is rotated toward the mandrel 160, the straight portion will contact the top of the mandrel and push down on it. Because the straight portion 316 is cantilevered to the body of the spring lever 234, and further is connected to the coiled portion 320, overrotation of the motor 232 merely results in additional downward force being transmitted to the mandrel 160. In this manner, the mandrel 160 can be held down onto the bearings 240, and more specifically into the V-grooves 280 of the bearings, thus accurately positioning the carrier 230 on the carriage 222, while still permitting the carrier to rotate in the bearings.

FIG. 9 also illustrates that it is advantageous when the lateral position of each spring lever 234 lines up with a space 310 along the mandrel 160 on which no workpiece 10 is mounted, thus preventing contact between the portion 316 and the delicate workpiece. Further advantageously, as suggested in FIG. 5, the lateral position of some or all of the spring levers 234 is made to also line up with a bearing 240, so that the force transmitted to the mandrel 160 is essentially a clamping force, and does not generate any bending moments that would distort the shape of the mandrel.

FIGS. 11-22 illustrate, in a highly schematic manner, exemplary processes embodying principles of the present invention of moving a carrier 230 through one or more processing substations; in this example, the workpiece 10 borne by the carrier is a tubular implantable medical device that has been mounted around the mandrel 160 of the carrier. The present invention is not limited to such workpieces, as discussed in greater detail below. Furthermore, because nearly all of the reference numerals used in FIGS. 1-22 have already been discussed, redundant recitals of these numbers will not be included so as to not obscure the invention. FIGS. 11, 13, 15, 17, 19, and 21 schematically illustrate a top plan view of portions of the processing station 200, while FIGS. 12, 14, 16, 18, 20, and 22 schematically illustrate side elevations views of the same subject matter, respectively.

Figure 11:
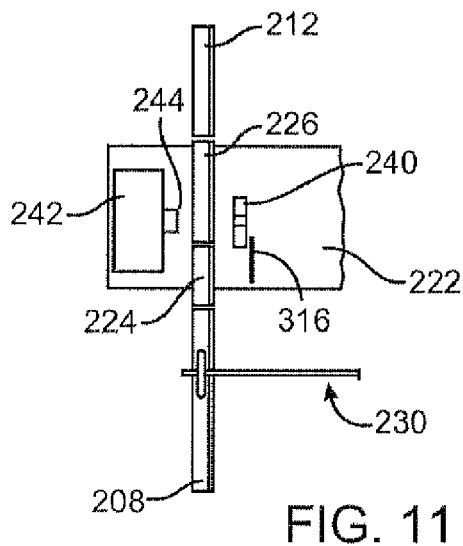
FIGS. 11-22 illustrate highly simplified views of a sequence of steps in an exemplary process in accordance with the present invention, in which the evenly numbered figures are side elevational views and the oddly numbered figures are corresponding top plan views.
Figure 12:
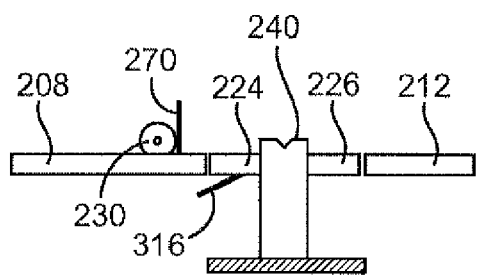

In FIGS. 11 and 12, a carrier 230 has rolled to the singulator 270, and has been stopped there. The straight portion of the spring lever 316 is retracted out of the way, and bearings are empty of another carrier.

Figure 13:
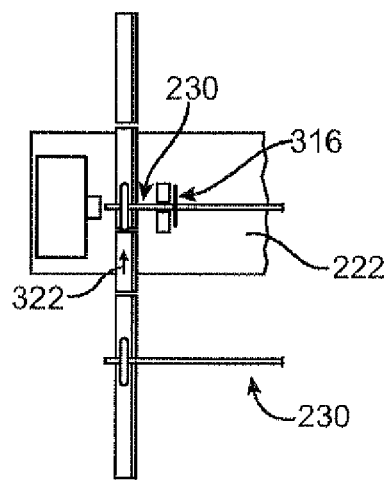
Figure 14:
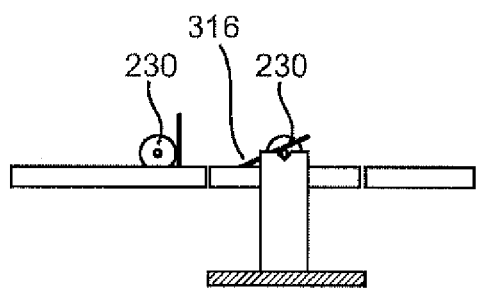

In FIGS. 13 and 14, the singulator has been actuated to permit a carrier to roll, per arrow 322, to a location where the pick-off arm generally positions the mandrel on or over the bearings 240. Another carrier has rolled up to the singulator, for release next. The straight portion 316 has been rotated into contact with the mandrel, thus holding down the carrier in the bearings. Thus, the carrier is very precisely located on the carriage.

Figure 15:
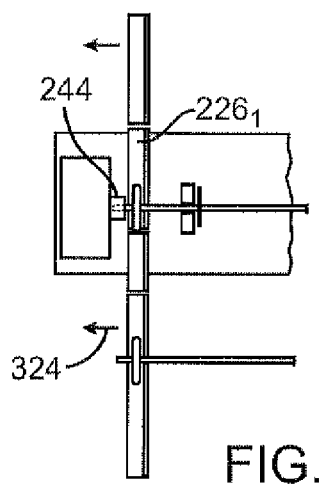
Figure 16:
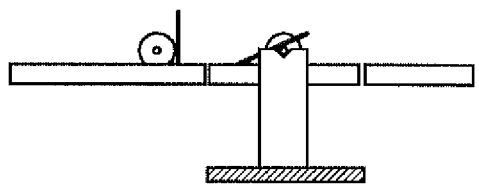

In FIGS. 15 and 16, the rail 226 has been moved laterally, indicated by arrow 324, relative to the chuck 244 so that the free end of the mandrel is now grasped by the chuck. The carrier is, at this point, precisely secured to the carriage, and is precisely rotatable in the bearings by the motorized chuck.

Figure 17:
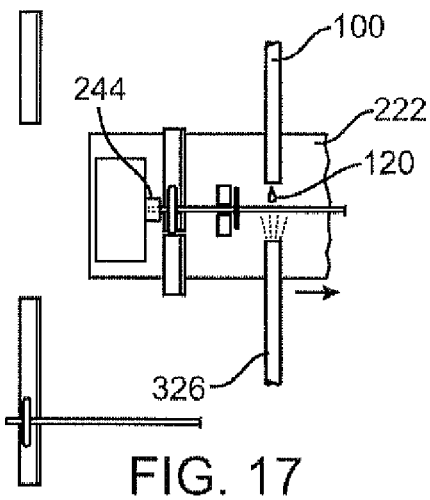
Figure 18:
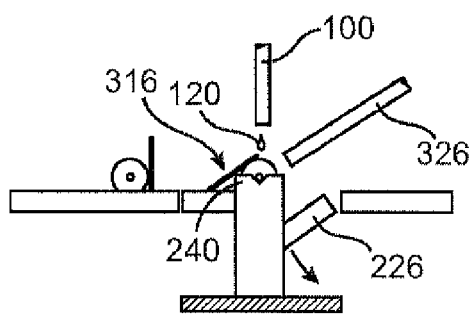

In FIGS. 17 and 18, the carriage 222 is moved laterally (to the right, as suggested by the arrow) into alignment with an apparatus to perform an operation on the workpiece (e.g., the dispenser 100 for deposition of a droplet into or onto the workpiece) mounted on the carrier; while in this example the dispenser is discussed, other processing devices can be used and the present invention is not limited to the use of a dispenser device. The pick-off arm has been rotated and lowered away, so that the carrier is supported only by the bearings, further assuring that they are accurately positioned. A vision system 326 collects image data of the location of the openings for deposition of droplets. The openings are then loaded with beneficial agent by simultaneously moving the carriage laterally to position different portions of the workpiece or workpieces mounted on the carrier in alignment with the dispenser, while the motorized chuck selectively rotates the carrier for the same purpose.

Figure 19:
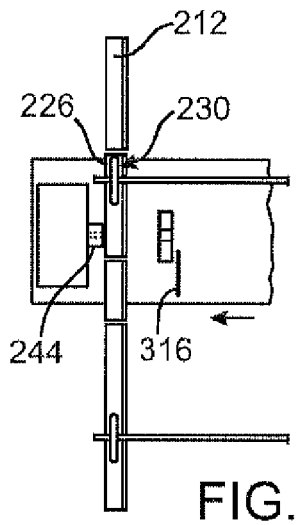
Figure 20:
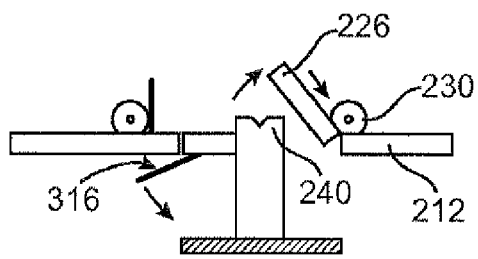

In FIGS. 19 and 20, after processing of the workpiece by the, e.g., dispenser, the carriage is moved back to the left, the straight portion 316 has been rotated off of the mandrel, the chuck has been actuated to release the free end of the mandrel, and the rail $226_2$ pulls the mandrel out of the chuck 242. The pick-off arm is rotated up, which causes the pick-off arm to lift the carrier by, e.g., one or more of its wheels, off of the bearings. The carrier is then free to roll, as suggested by the arrow in the drawing, out of the processing substation.

Figure 21:
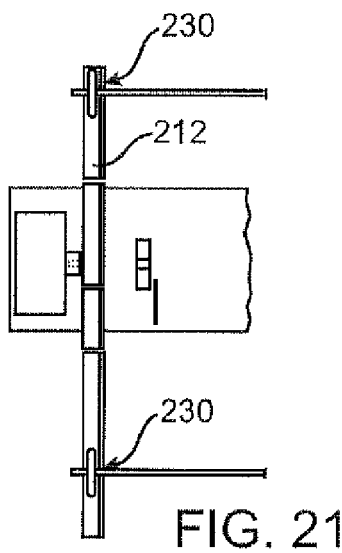
Figure 22:
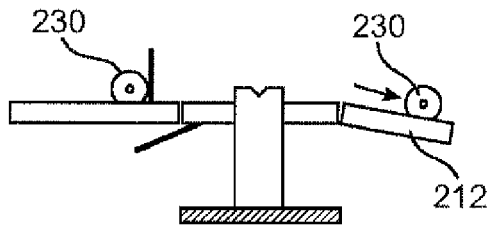

In FIGS. 21 and 22, the carrier has rolled into the output substation and continues to roll, as suggested by the exaggerated downward slope angle thereof, illustrated in FIG. 22; FIGS. 12-20 do not show this slope merely for ease of illustration, so as to not obscure aspects of the invention. At this point, the processing station is ready to receive the next carrier for processing.

Figure 23:
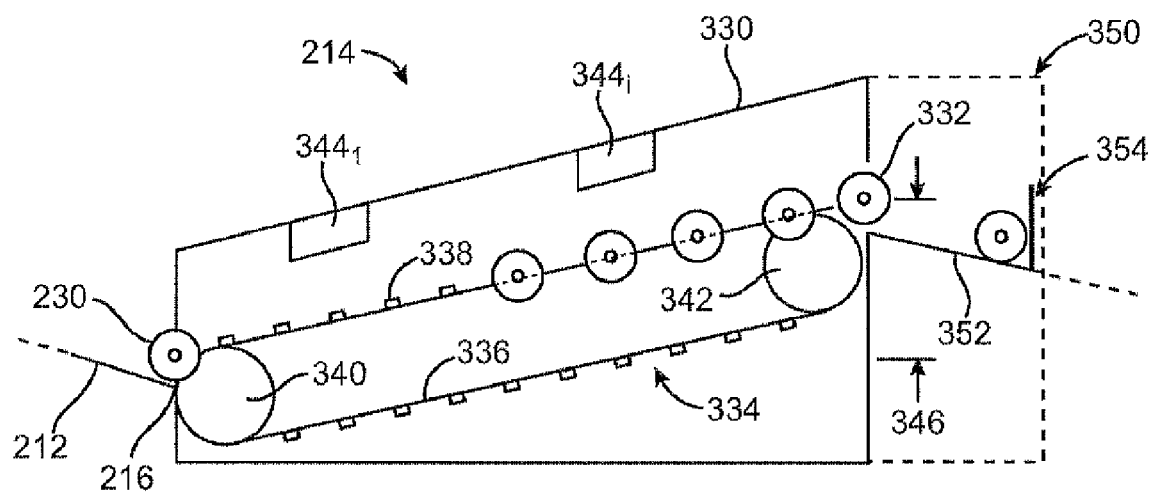
FIG. 23 illustrates a cross-sectional view of an elevator embodying principles of the present invention.

Turning now to FIG. 23, an exemplary elevator 214 is illustrated. The elevator preferably, albeit optionally, includes a housing 330 in which the input opening 216 and an output opening 332 are formed, A conveyor 334 is positioned to extend between the openings 216, 332. The conveyor 334 includes an endless belt, or the like, 336 equipped with ribs, hooks, fingers, depressions, or other structure 338 which are configured to push or pull a carrier on the conveyor as the carrier is moved by the elevator 330. The conveyor 334 also includes two or more drives and/or followers 340, 342, around which the belt 336 is looped and which moves the belt in a known manner.

The conveyor 334 is positioned in the elevator 330 so that there is a height difference 346 between the openings 216, 332, and more particularly so that the output opening 332 is higher than the input opening 216. In this manner, when a carrier 230 rolls down the rail 212 of the output substation 206, it enters the elevator 330 at input opening 216, is held on the belt 336 by the structure 338 from rolling back, and is conveyed and elevated up to the output opening 332.

In addition to merely acting to increase the elevation of a carrier 230, the elevator 330 can optionally include one or more processing devices $344_i$ positioned over the belt 336 so that the processing devices can be used to further process the workpieces 10. The processing devices $344_i$, when provided, can include one or more of heaters, driers, gas jets, liquid jets, radiation sources, including light sources, and the like. When provided with the one or more processing devices $344_i$, the elevator 330 functions as a processing substation as well. Advantageously, the processing devices $344_i$ include one or more driers to dry the beneficial agents that have been deposited onto the workpiece. The elevator can be enclosed with a suitable housing for environmental control.

FIG. 23 also illustrates an optional staging device 350, connected to the output opening 332. The staging device 350 preferably includes two or more rails 352, configured as the other rails described herein, to receive the wheels 250 of the carriers 230. A further optional dispensing device 354, which may be a singulator, is positioned to control the outflow of carriers 230 from the staging device 350 on to further optional processing stations and substations (not illustrated).

The present invention is not restricted to the particular embodiments described above, and different apparatus and methods are also within the scope of the present invention. For example, the singulator can be configured as one or more rotating arms, rather than a pair of linearly movable racks, which operate as a 'toll gate' to control the flow of carriers. Further optionally, the singulator can be configured to contact the carrier on one or more of the wheels of the carrier.

As discussed above, the workpiece is not limited to the particular implantable medical devices discussed herein. Instead of the unique implantable medical device illustrated in FIG. 1, the workpiece can instead be a more primitive cardiovascular stent which is to be processed to include one or more exterior surface coatings, optionally including one or more beneficial agents. For processing such surface coated, drug eluting stents, individual drops of coating may be less preferable, and instead one or more spray heads can replace the microjet to spray the exterior surface of the device.

In addition to processing less sophisticated implantable medical devices, systems and methods of the present invention can operate on workpieces that are not purely tubular. For example, the mandrel can have a non-circular (e.g., rectangular, square, triangular) cross-section, and the workpieces can be securely, yet temporarily, mounted (e.g., glued) to a portion of the 'circumference' of the mandrel, e.g., to a face of the non-circular mandrel. In this manner, other devices can be processed in accordance with the present invention, such as devices that are not shaped to be mounted around a mandrel.

The foregoing descriptions and illustrations detail a generally horizontally-oriented process flow; however, the present invention is not so limited. Instead of being generally horizontal, the several substations can be, essentially, stacked one on the other, with the rails of each substation oriented in the shape of a "Z". In this configuration, carriers are still free to rely on gravity to roll through the one or more serially disposed processing substations, but the serial configuration is more vertical and less horizontal. In this vertical configuration, it may be possible to eliminate the elevator, while still retaining all of the processing functions, including drying, that may be incorporated into an elevator. Such a vertical configuration can have a much smaller footprint than the horizontal configuration, but also, less preferably, is more difficult to swap out substations for maintenance. The various stations and substations can be modular, replaceable, and interchangeable for ease in changing the manufacturing process, upgrading, maintenance, and the like.

Figure 24:
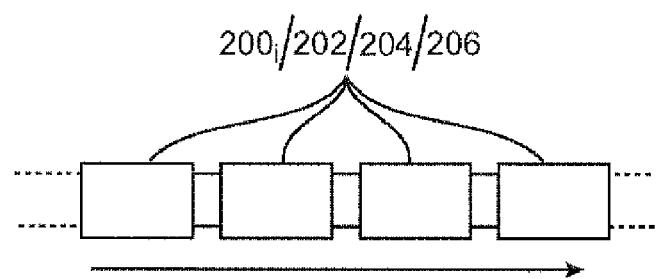
FIG. 24 diagrammatically illustrates a series of processing stations and/or substations in accordance with the present invention.

With reference to FIG. 24, it is also a part of the present invention that one or more processing stations $200_i$ can be serially connected so that a plurality of processing steps, whether the same or different, can be conducted on workpieces borne by carriers 230. Furthermore, as it may not be necessary to further elevate or process the workpieces within a housing, such as housing 330, after each processing substation 204, the elevator 214 can be selectively omitted along a series of one or more processing substations, and an elevator 214 provided only at intervals along the series. Furthermore, one or more singulators can be provided between each processing stations $200_i$, as well as sets of rails to receive carriers 230 from and lead carriers to each processing station or substation.

An example of a processing station 200, with general reference to FIG. 24, will help further describe some aspects of the present invention. A processing station 200 which can produce a five-layer deposit in an opening 60 of a medical device 10 (see FIG. 2) includes an input substation 202, an output substation 206, and five serially connected processing substations 204 positioned between the input and output substations. Preferably, one or more drying, etc., devices 344, which may be embodied in elevators 214 or provided in a housing which does not further elevate the carriers 230, are optionally provided serially after each processing substation 204, for the purposes described elsewhere herein. Each of the processing substations 204 is equipped to deposit a selected amount of a selected material into the opening 60. By way of non-limiting example, the series of processing substations 204 are equipped to sequentially deposit the following layers: a polymer-only base; a first, therapeutic-agent-and-polymer layer; a second, therapeutic-agent-and-polymer layer; a third, therapeutic-agent-and-polymer layer; and a polymer-only cap.

With reference to FIGS. 7 and 8c, one exemplary embodiment of the present invention includes wheels 250 of a carrier 230 riding on surfaces 260, in which the rails include inner bearing guides 262. In another exemplary embodiment of the present invention, these elements are reversed. More specifically, the rails are shaped as the wheels 250, and the wheels include the bearing surfaces 262, somewhat like the configuration of traditional railroad wheels and rails.

According to yet another exemplary embodiment, each carrier 230 is provided with an identification device or mark. By way of non-limiting example, such an ID device can include one or more of: an RFID tag; a one-dimensional bar code; and a two-dimensional bar code. Preferably, the ID device is located in, or on an external surface of, one or both of the wheels 250, so as to be readable by an appropriate reader to identify the specific carrier within the processing system.

According to further exemplary embodiments of the present invention, the conveyance of the carriers 230 through the processing substations is performed, in addition to or instead of gravity feed, by one or more of the following: conveyor belts; a mandrel-only based conveying system; magnetic feeding; compressed air feeding; and robotic arms. Other forms of conveying systems can be incorporated into a processing system of the present invention.

While the invention has been described in detail with reference to exemplary embodiments thereof it will be apparent to one skilled in the art that various changes can be made, and equivalents employed, without departing from the scope of the invention. The foregoing description of the preferred embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principles of the invention and its practical application to enable one skilled in the art to utilize the invention in various embodiments as are suited to the particular use contemplated. It is intended that the scope of the invention be defined by the claims appended hereto, and their equivalents. The entirety of each of the aforementioned documents is incorporated by reference herein.

What is claimed is:

1. A method of processing a medical device, the method comprising:
    performing a first operation (A) or (B) on at least one medical device mounted on at least one mandrel at a first location, wherein
        operation (A) comprises depositing a material onto or into the at least one medical device, and
        operation (B) comprises a process selected from the group consisting of drying, irradiating, heating, and combinations thereof;
    automatically transporting said at least one mandrel to a second location with a conveyance system; and
    performing a second operation (A) or (B) on said medical device at said second location wherein the at least one mandrel comprises at least two wheels mounted on each end of the at least one mandrel.

2. A method according to claim 1, wherein said material comprises a beneficial agent.

3. A method according to claim 1, further comprising:
    elevating said at least one medical device during or after said second operation.

4. A method according to claim 1, wherein depositing a material comprises selectively depositing drops of material.

5. A method according to claim 4, wherein depositing a material comprises depositing at least one drug.

6. A method according to claim 1, wherein depositing a material comprises coating the exterior of the medical device.

7. A method according to claim 1, wherein automatically transporting comprises gravity feeding.

8. A method according to claim 7, wherein gravity feeding comprises rolling the medical device by gravity.

9. A method according to claim 7, wherein gravity feeding comprises rolling the at least one mandrel by gravity.

10. A method according to claim 9, wherein the at least one mandrel comprises at least two wheels, and rolling the at least one mandrel comprises rolling said at least two wheels on a sloped surface.

11. A method according to claim 7, wherein gravity feeding comprises gravity feeding in a first direction, and further comprising:
    moving said at least one medical device in a second direction different from said first direction
        before said performing a first operation (A) or (B), or
        before said performing a second operation (A) or (B), or
        before both.

12. A method according to claim 1, wherein the at least one medical device comprises a stent.

13. A method according to claim 1, wherein the at least one medical device comprises at least one opening, and wherein depositing a material onto or into the at least one medical device comprises depositing at least a therapeutic agent into said at least one opening.

14. A method according to claim 1, further comprising:
    repeating said performing a first operation (A) or (B).

15. A method according to claim 1, wherein automatically transporting comprises transporting with a conveyance system comprising a device selected from the group consisting of a conveyor belt, a magnetic conveyor, an air compressor, and a robotic device.

16. A method according to claim 1, wherein the at least one implantable medical device is positioned between two of the at least two wheels.

17. A method according to claim 1, wherein the at least one mandrel comprises a free end which extends past one of the at least two wheels.

18. A method according to claim 1, wherein the at least one mandrel comprises a jacket, the at least one medical device positioned on the jacket.

19. A method according to claim 1, wherein the at least one medical device comprises a plurality of implantable medical devices mounted on the at least one mandrel in a spaced relationship with at least one gap therebetween.

20. A method according to claim 1, wherein automatically transporting comprises singulating the at least one mandrel.

21. A method according to claim 1, wherein automatically conveying comprises separately conveying the at least one mandrel in first and second directions which are mutually orthogonal.

22. A method according to claim 1, wherein automatically conveying comprises conveying along a slope.

* * * * *